(12) United States Patent
Ichihara et al.

(10) Patent No.: US 9,038,474 B2
(45) Date of Patent: May 26, 2015

(54) PHOTOACOUSTIC MEASURING APPARATUS (75) Inventors: Shigeru Ichihara, Tokyo (JP); Shuichi Kobayashi, Yokohama (JP)

(73) Assignee: CANON KABUSHIKI KAISHA, Tokyo (JP)

( * ) Notice: Subject to any disclaimer, the term of this patent is extended or adjusted under 35 U.S.C. 154(b) by 345 days.

(21) Appl. No.: 13/582,028

(22) PCT Filed: Apr. 22, 2011

(86) PCT No.: PCT/JP2011/002383
§ 371 (c)(1),
(2), (4) Date: Aug. 30, 2012

(87) PCT Pub. No.: WO2011/135820
PCT Pub. Date: Nov. 3, 2011

(65) Prior Publication Data
US 2012/0318066 A1    Dec. 20, 2012

(30) Foreign Application Priority Data

Apr. 26, 2010    (JP) .................................. 2010-101006

(51) Int. Cl.
*G01N 21/17*    (2006.01)
*G01N 29/34*    (2006.01)
(Continued)

(52) U.S. Cl.
CPC ............. *A61B 5/0073* (2013.01); *A61B 5/0095* (2013.01); *G01N 21/1702* (2013.01)

(58) Field of Classification Search
USPC .................... 73/655, 656, 641, 632, 643, 596; 600/407; 356/432
See application file for complete search history.

(56) References Cited

U.S. PATENT DOCUMENTS 7,548,309 B2 * 6/2009 Kusunose et al. ........... 356/237.2
2006/0184042 A1 * 8/2006 Wang et al. ................... 600/476
(Continued)

FOREIGN PATENT DOCUMENTS

JP       2010-017426      1/2010
WO   WO 2009/154298 A1   12/2009
(Continued)

OTHER PUBLICATIONS

S. Manohar et al., "The Twente Photoacoustic Mammoscope", *Physics in Medicine and Biology*, vol. 50, No. 11, pp. 2543-2557 (May 18, 2005).

(Continued)

*Primary Examiner* — Helen Kwok
(74) *Attorney, Agent, or Firm* — Fitzpatrick, Cella, Harper & Scinto (57) ABSTRACT

The present invention employs a photoacoustic measuring apparatus including: a laser light source; a forming unit for forming a second light beam by dividing or deforming a laser light beam; an optical member for guiding the second light beam to the surface of a subject; a probe for obtaining a photoacoustic wave generated when the subject is irradiated with the second light beam; and a buffering member that contacts the surface of the subject and transmits light, wherein the optical member overlaps areas of the second light beam having a small light intensity on the surface of the subject, the probe and the optical member are positioned on an identical side of the buffering member relative to the subject, and the optical member refracts the second light beam such that the second light beam enters the subject through the buffering member while avoiding the probe.

6 Claims, 5 Drawing Sheets

(51) Int. Cl.
  *G01H 9/00*   (2006.01)
  *A61B 5/00*   (2006.01)

(56)        References Cited

U.S. PATENT DOCUMENTS

| | | | |
|---|---|---|---|
| 2007/0299341 A1 | 12/2007 | Wang et al. | 600/443 |
| 2009/0005685 A1* | 1/2009 | Nagae et al. | 600/459 |
| 2009/0040754 A1* | 2/2009 | Brukilacchio et al. | 362/228 |
| 2010/0319453 A1 | 12/2010 | Ichihara et al. | 73/596 |
| 2011/0088477 A1* | 4/2011 | Someda et al. | 73/641 |
| 2011/0102797 A1 | 5/2011 | Ichihara et al. | 356/445 |
| 2011/0112391 A1* | 5/2011 | Nishihara et al. | 600/407 |
| 2011/0303015 A1 | 12/2011 | Ichihara et al. | 73/656 |
| 2012/0179022 A1 | 7/2012 | Ichihara et al. | 600/407 |

FOREIGN PATENT DOCUMENTS

| | | |
|---|---|---|
| WO | WO 2010/005109 A1 | 1/2010 |
| WO | WO 2010/005116 A1 | 1/2010 |

OTHER PUBLICATIONS

J.J. Niederhauser et al., "Combined Ultrasound and Optoacoustic System for Real-Time High-Contrast Vascular Imaging in Vivo", *IEEE Transactions on Medical Imaging* vol. 24, No. 4 (Apr. 1, 2005).

* cited by examiner

PHOTOACOUSTIC MEASURING APPARATUS

TECHNICAL FIELD

The present invention relates to a photoacoustic measuring apparatus for obtaining and forming an image of information relating to a subject.

BACKGROUND ART

In recent years, photoacoustic tomography, in which an optical characteristic value distribution of an organism interior is determined in high definition using a characteristic of an acoustic wave (typically an ultrasound wave) that produces less scattering in the organism interior than light has been proposed. In this specification, photoacoustic tomography is referred to as PAT. When an organism is irradiated with pulsed light generated by a light source, the pulsed light propagates through the organism interior while diffusing. Photoabsorbers contained in body tissue absorb energy from the propagated pulsed light and generate an acoustic wave. By subjecting a resulting acoustic wave signal to analysis processing, an optical characteristic distribution of the organism interior, and in particular an optical energy absorption density distribution, can be obtained.

A photoacoustic mammography (to be referred to in this specification as PAM) apparatus has been proposed as an apparatus for applying PAT to an organism. A PAM apparatus detects the position of a breast tumor by forming an image of new blood vessels formed on the periphery of the tumor during tumorigenesis and areas having a high absorption coefficient and including the new blood vessels. To diagnose an entire breast, it is important not only to obtain a high definition image, but also to shorten a diagnosis time by widening a measurement area per measurement operation.

A PAM apparatus is mainly constituted by an illumination optical system serving as an input system and an ultrasound wave detection system serving as an output system. Various constitutions have been proposed for the illumination optical system up to the present day. In a rear detection type photoacoustic apparatus in which the illumination optical system and the ultrasound wave detection system are disposed on an identical side, a dark field illumination optical system for observing a superficial site of an organism surface has been proposed as a photoacoustic wave microscope (see U.S. Patent Application Specification No. 2006/0184042, hereinafter called PTL 1). An illumination optical system that inputs light beams from both sides of a linear array ultrasound probe has also been proposed (see Joel J. Niederhauser, Michael Jaeger, Robert Lemor, Peter Weber, and Martin Frenz, IEEE TRANSACTIONS ON MEDICAL IMAGING, vol. 24, no. 4, 436, hereinafter called NPL 1).

CITATION LIST

Patent Literature

[PTL 1]
U.S. Patent Application Specification No. 2006/0184042

Non Patent Literature

[NPL 1]
Joel J. Niederhauser, Michael Jaeger, Robert Lemor, Peter Weber, and Martin Frenz, IEEE TRANSACTIONS ON MEDICAL IMAGING, vol. 24, no. 4, 436

SUMMARY OF INVENTION

Technical Problem

In a photoacoustic mammography (PAM) apparatus, it is important to increase the intensity of a photoacoustic signal (a PA signal) in order to increase the definition of the diagnosis while reducing the diagnosis time by widening the measurement area per measurement operation. The signal intensity of the PA signal increases as the amount of radiation applied to the photoabsorber part of the organism interior is increased. However, there are limits to a maximum permissible exposure (MPE) that can be applied to the organism surface. One of these limits is described in "Safety Guidelines for Laser Products and their Users" from 60825-1 of the International Electrotechnical Commission, abbreviated to IEC). Another limit is described in "Safety Standards for Laser Products" from JIS C 6802 of Japanese Industrial Standards (JIS), which conforms to the IEC. The MPE is a maximum irradiance value, i.e. a maximum amount of radiation per unit surface area. To obtain a large PA signal using a PAM apparatus, the entire illumination area of the organism surface is preferably illuminated evenly with irradiance no greater than the MPE.

In a rear detection type PAT apparatus in which the illumination optical system and the ultrasound wave detection system are disposed on the same side, the ultrasound probe obstructs to a light beam transmission path. Therefore, an illumination optical system that performs illumination while avoiding the ultrasound probe has been proposed, as described in PTL 1 and NPL 1. PTL 1 employs dark field illumination in which an ultrasound probe front surface is not irradiated, and as a result, a light intensity distribution of the illumination area is uneven. The illumination optical system disclosed in NPL 1 performs illumination by reflecting a light intensity distribution of a light beam on the organism surface. Therefore, when the distribution of a light beam emitted from the light source is uneven, evenness cannot be achieved in the light intensity distribution on the organism surface.

An image display apparatus such as a projector has been proposed many times as a method of making an illumination distribution even. However, the radiation amount thereof differs greatly from that of an illumination optical system used in a PAM apparatus. Moreover, a PAM apparatus is used specifically together with an ultrasound probe. In other words, in a rear detection type PAM apparatus using a light source that generates a light beam having an uneven light intensity distribution, a total emitted light amount is maximized by reducing a light intensity distribution difference over the entire illumination area of the organism in order to improve the illumination evenness.

The present invention has been designed in consideration of the problems described above, and a subject thereof is to provide a technique for reducing a light intensity distribution difference occurring on an organism surface when the organism surface is irradiated with light in a photoacoustic measuring apparatus that uses laser light.

Solution to Problem

This invention provides a photoacoustic measuring apparatus comprising:
a light source which emits laser light;
a forming unit which forms a second light beam by dividing or deforming a light beam of the laser light;
an optical member which guides the second light beam to an irradiation area on a surface of a subject;

a probe which obtains a photoacoustic wave generated from the subject when the subject is irradiated with the second light beam; and a buffering member which contacts the surface of the subject and transmits the light, wherein the optical member emits the second light beam onto the surface of the subject such that areas of the second light beam having a small light intensity overlap, the probe and the optical member are positioned on an identical side of the buffering member relative to the subject, and the optical member refracts the second light beam such that the second light beam enters the subject through the buffering member while avoiding the probe.

Advantageous Effects of Invention

According to the present invention, a light intensity distribution difference occurring on an organism surface when the organism surface is irradiated with light can be reduced in a photoacoustic measuring apparatus that uses laser light.

Further features of the present invention will become apparent from the following description of exemplary embodiments with reference to the attached drawings.

DESCRIPTION OF EMBODIMENTS

Preferred embodiments of the present invention will be described below with reference to the drawings. Principle constitutional elements of a photoacoustic measuring apparatus to be described below are an illumination optical system for illuminating a subject by guiding light from a light source thereto, and a photoacoustic wave detection system for detecting a photoacoustic wave generated from a photoabsorber in the interior of the subject. Note that dimensions, materials, and shapes of constitutional components to be described below, as well as positional relationships therebetween and so on, may be modified appropriately in accordance with the constitution of the apparatus to which the present invention is to be applied and various conditions, and the scope of the present invention is not limited to the following description. In the following description, a living organism is used as an example of the subject, but the present invention is not limited thereto.

This apparatus in particular is applied to breast diagnosis, and an aim thereof is to measure an organism interior over a wide range. To measure a wide range efficiently, a measurement area per measurement must be widened. This can be achieved effectively by widening an illumination area of a breast surface and using a two-dimensional array type ultrasound probe to obtain a photoacoustic wave.

Further, to obtain an accurate diagnosis, a photoacoustic signal from a photoabsorber positioned in a deep portion of the organism must be detected, and this can be achieved effectively by increasing the irradiance on the organism surface so that high photoacoustic signal intensity is detected. However, the irradiance of the laser light on the organism surface is limited to the maximum permissible exposure (MPE). It is therefore most effective to maximize a total emitted light amount emitted onto the organism by illuminating the illumination area evenly with irradiance no greater than the MPE.

However, there is a limit to the output energy of the light source. Hence, in the following embodiments, a method of making illumination even that employs a comparatively simple illumination optical system, exhibits favorable energy efficiency, and results in little energy loss occurs will be described. Hereafter, the term "making illumination even" means reducing a light intensity distribution difference in the interior of the illumination area in comparison with a case where the organism surface is illuminated by a light intensity distribution conforming to the light intensity distribution of the light source, and is not limited to illumination of the entire illumination area with perfectly even irradiance.

In the photoacoustic measuring apparatus according to the following embodiments, an ultrasound probe and the illumination optical system for irradiating the illumination area of the organism surface with light are disposed on an identical side relative to the organism. Note, however, that the ultrasound probe and the illumination optical system are not limited to this arrangement. Use of the present invention to even out the light amount while satisfying the MPE does not depend on the direction of the illumination area, and as long as a laser is used, any constitution may be employed. However, a constitution in which the ultrasound probe and the illumination area for illuminating the organism surface are disposed on the same side relative to the organism typically corresponds to a constitution in which a laser beam is divided, and therefore this constitution may be used. In other words, a constitution for dividing a beam and a constitution for making a light intensity even are combined.

Figure 1:
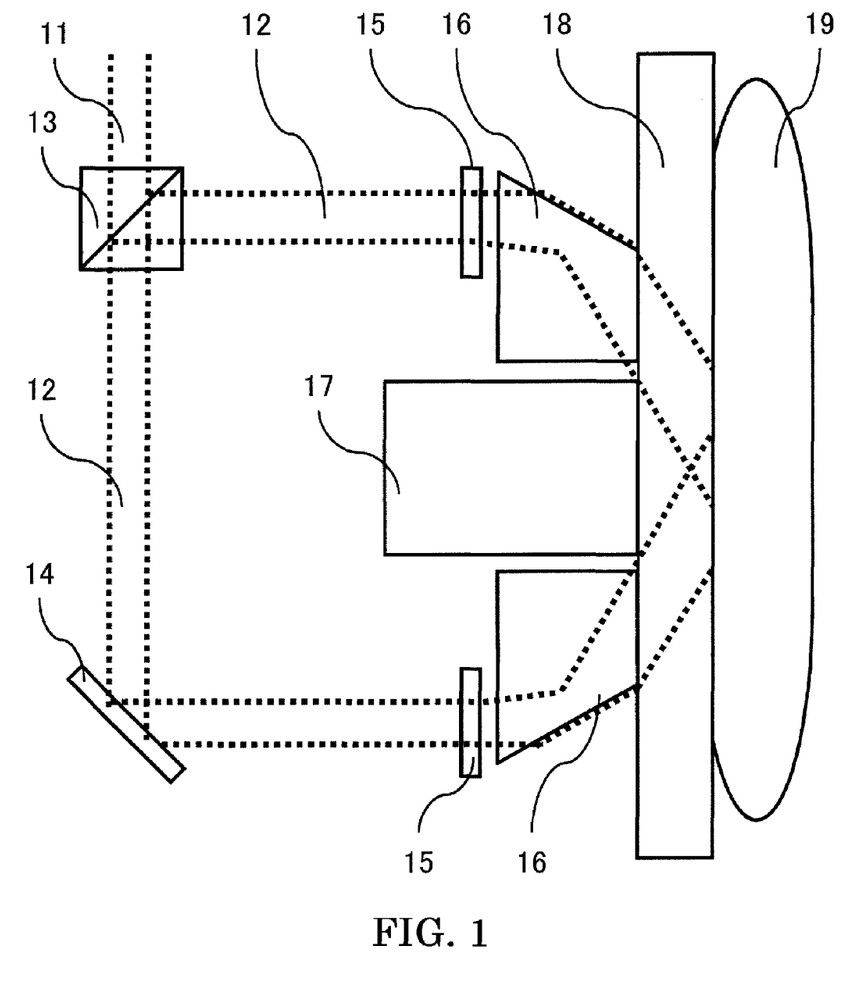
FIG. 1 is a schematic view showing the constitution of an apparatus according to a first embodiment.

The above constitution in which the ultrasound probe and the illumination range are on the same side is known as a rear detection arrangement. An apparatus shown in FIG. 1 also has a rear detection arrangement. In FIG. 1, a light beam is emitted onto an organism 19 from the same side as an ultrasound probe 17 and a buffering member 18. In contrast to this arrangement, an arrangement in which the ultrasound probe and the illumination range oppose each other on either side of the organism to be measured is known as a front detection arrangement. In an apparatus having a front detection arrangement, the ultrasound probe does not obstruct light beam transmission, and therefore the illumination light can be made even comparatively simply. With a rear detection arrangement, on the other hand, the illumination must be made even by transmitting the light beam while avoiding the ultrasound probe. Further, with a rear detection arrangement, the laser beam is divided in order to avoid the ultrasound probe, and as a result, the entire surface of the organism corresponding to the ultrasound probe is irradiated with divided laser light. Note that with a constitution in which the laser light is not divided and the organism is irradiated with light from a single direction while avoiding the ultrasound probe, it is difficult to irradiate the entire organism surface corresponding to the ultrasound probe with light.

In a breast diagnosis, the rear detection arrangement and the front detection arrangement described above may be combined, and for convenience, a resulting arrangement will be referred to as a double-sided irradiation arrangement. In an apparatus employing the double-sided irradiation arrangement, buffering members are disposed to sandwich the organism from either side. The ultrasound probe is disposed on one buffering member, and light is emitted from the optical system so as to avoid the probe. The optical system is disposed on the other buffering member. The illumination method of the present invention may be employed on the side where the probe is disposed.

Laser light pulse-generated at no more than approximately 100 ns is preferably used as the light source. A pulse laser exhibiting high output energy is particularly favorable for diagnosing an entire breast. A light beam distribution of a pulse laser most often takes a Gauss shape in which the light intensity in a central part of the light beam is greatest or a flat top shape in which the Gauss shape is made slightly more uniform. In the present invention, light beams having uneven light intensity distributions emitted from two or more types of light sources may be used. In other words, according to the present invention, a light intensity distribution difference over the illumination area of the organism surface can be reduced using laser light having an uneven light intensity distribution. The light beam can be made even using bundle fiber, but in this case, energy loss at an input end is high, leading to problems such as a reduction in energy efficiency.

A method of making a light beam even according to the present invention is implemented through the following steps.

In a first step, a light beam emitted from a light source having an uneven light intensity distribution is divided (bifurcated) or deformed using an optical member (a forming unit) to form a second light beam. When laser light is divided (bifurcated), a plurality of second light beams can be formed. Depending on the employed optical member, second light beams divided (bifurcated) and deformed in various ways may be formed. These various forms will be described in detail below.

In a second step, the second light beams are transmitted while avoiding an ultrasound probe positioned near the organism so as to enter the organism surface from an outer side of the ultrasound probe. In the second step, the second light beams are transmitted toward the organism surface using a reflection optical member. By making appropriate use of the reflection optical member, the second light beams can be emitted onto the organism surface while controlling a light intensity distribution position.

In a third step, an illumination area is created on the organism surface by overlapping areas of the second light beams in which the light intensity distribution is small. In the third step, an optical wave guide buffering member having a constant thickness is required to guide the second light beams to the organism surface positioned on a front surface of the ultrasound probe. A member that transmits laser light and exhibits little ultrasound wave transmission loss, for example a resin member made of polymethyl pentene or the like, may be used as the buffering member. The light beam must be bifurcated or deformed not only to avoid the ultrasound probe, but also so that the light beams can be overlapped on the organism surface. By overlapping parts of the bifurcated or deformed second light beams having a small light intensity, the light intensity distribution difference in the illumination area of the organism surface is reduced. To achieve evenness, a value of the light intensity in the overlapped part of the light intensity distribution in the irradiation area following overlapping is preferably equal to a maximum light amount value of the second light beam, or more specifically within a range from 90 percent of the maximum value to the maximum value. Therefore, in the third step, areas in which the light intensity is no more than half the maximum value of the light intensity distribution of the second light beam are preferably overlapped.

The method of making a light beam even according to the present invention differs from that of an illumination optical system employing a fly eye lens, which is often seen in image display apparatuses such as projectors. With a fly eye lens, the light intensity distribution is made even by overlapping all bifurcated light beams in an identical area. With this method, an extremely high degree of evenness is obtained, but since the light beams are converged by the fly eye lens, the method is not appropriate for PAM, which uses a large intensity of pulse energy. Other possible methods of solving this problem include enlarging the light beam in order to reduce an energy density and then evening out the light beam using a fly eye lens. However, with this method, problems such as increases in the size of the optical system and the cost of the employed optical members occur.

(First Embodiment)

FIG. 1 is a schematic view of this embodiment. In the drawing, an emitted light beam 11 and bifurcated light beams 12 are shown as light beams. In the drawing, outer edges of the light beams are indicated by dotted lines. Further, a bifurcation beam splitter 13, a reflection mirror 14, a light diffusion plate 15, and a reflection trapezoidal prism 16 are provided as an optical system. Furthermore, an ultrasound probe 17 and a buffering member 18 are disposed to contact an organism 19. A high-energy pulse laser is used as a light source. This type of laser typically exhibits a light intensity distribution in which a large intensity of light exists in a central part of an emitted light beam. The shape of the light beam depends on the shape of a used laser oscillation medium but is often pseudo-circular. In this embodiment, the laser light described above is used, but the shape of the light beam and the light beam distribution is not limited thereto.

Here, a prism is used as the bifurcation beam splitter 13, but a flat plate beam splitter may be used instead. When the emitted light beam 11 is split by the bifurcation beam splitter 13, the energy from each of the two bifurcated light beams 12 is half that of the emitted light beam 11. The light intensity distribution is maintained such that a central part of each bifurcated light beam 12 has a high light intensity distribution.

The bifurcated light beams 12 pass through the light diffusion plate 15. Note that although the light diffusion plate 15 is used here, the light diffusion plate 15 does not have to be used. The utility of the light diffusion plate 15 will be described below. After passing through the light diffusion plate 15, the light beams are refracted by the reflection trapezoidal prism 16 and then caused to enter the organism 19 diagonally from either side so as to avoid the ultrasound probe 17. The buffering member 18 is positioned between the ultrasound probe 17 and the organism 19, and the illumination range of the organism surface varies in accordance with the thickness of the buffering member 18. In the drawing, inner sides of the respective bifurcated light beams enter the organism 19 in an overlapped fashion, as is evident from a central part of a contact surface between the organism 19 and the buffering member 18 in the drawing. The ultrasound probe 17 obtains a photoacoustic wave generated from the organism when illuminated. Variation in a light absorption coefficient of the organism interior is visualized by subjecting the photoacoustic wave to amplification and digital conversion using a signal processing device (not shown) and to image reconstruction using an information processing device, and this visualization is used in a diagnosis.

Figure 2A:
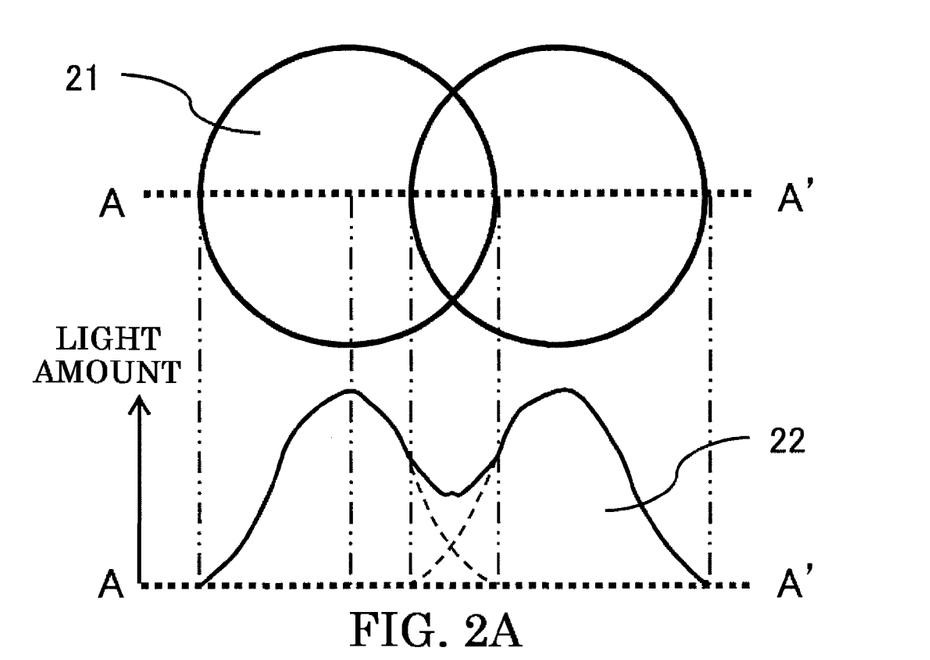
FIG. 2 is a view showing an illumination area and a light intensity distribution obtained when bifurcated light beams are overlapped.

FIG. 2A shows the illumination range and the light intensity distribution on the organism surface. Bifurcated light beams 21 are emitted onto the organism surface with a light intensity distribution 22 on a line A-A' as indicated on a graph. By overlapping the parts having a small light intensity in the light intensity distributions of the respective bifurcated light beams in this manner, the light intensity distribution difference in the illumination range is reduced in comparison with a case where such overlapping is not performed (a condition indicated by broken lines on the light intensity distribution 22). The amount of overlapping can be varied as desired in accordance with a position on the organism surface, or in other words the thickness of the buffering member 18. Further, by increasing the thickness of the buffering member 18 such that the respective bifurcated light beams 12 entering the organism 19 diagonally intersect in the interior of the buffering member 18, the overlapping position can be inverted. Note that a distance from the ultrasound probe to the organism surface is preferably short in order to reduce ultrasound wave transmission loss.

Figure 2B:
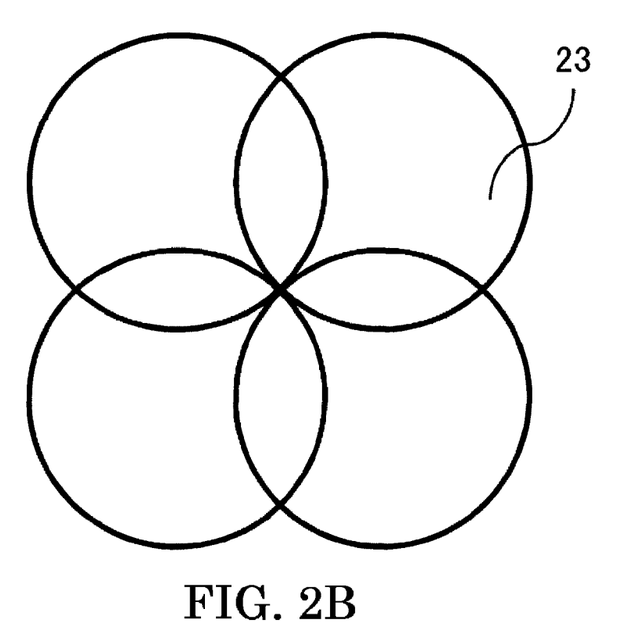

The light beam emitted from the light source may be bifurcated in more than two beams, and by employing a two-stage beam splitter, four bifurcated light beams can be obtained. FIG. 2B shows a case in which four bifurcated light beams 23 are overlapped on the illumination area of the organism surface. The present invention does not exclude the formation of bifurcated light beams divided into more than two beams.

(Second Embodiment)

Figure 3:
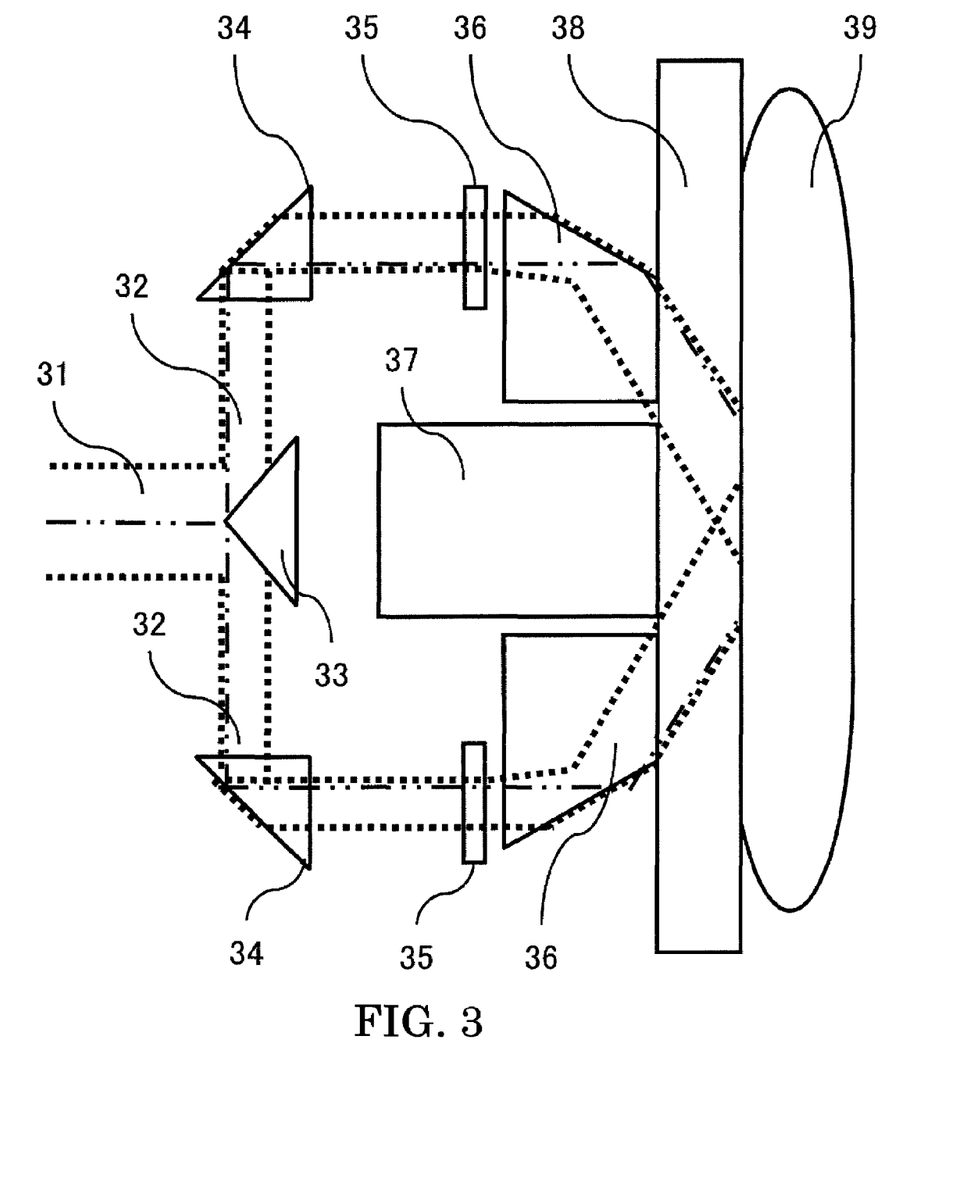
FIG. 3 is a schematic view showing the constitution of an apparatus according to a second embodiment.

FIG. 3 is a schematic view showing an apparatus according to this embodiment. In the drawing, an emitted light beam 31 and bifurcated light beams 32 are shown as light beams. Further, a bifurcation knife edge 45 degree right-angled reflection triangular prism 33 (a knife edge prism), a reflection prism 34, a light diffusion plate 35, and a reflection trapezoidal prism 36 are provided as an optical system. Furthermore, an ultrasound probe 37 and a buffering member 38 are disposed to contact an organism 39. A high-energy pulse laser is used as a light source. The emitted light beam is pseudo-circular and has a light intensity distribution in which a large intensity of light exists in a central part of the light beam. In the drawing, outer edges of the light beams are indicated by dotted lines and parts of the light intensity distribution having a large light intensity are indicated by dot-dot-dash lines.

When the part of the light beam 31 having a large light intensity enters a knife edge part of the bifurcation knife edge 45 degree right-angled reflection triangular prism 33, the light beam 31 is divided into two about the part having a large light intensity to form semicircular bifurcated light beams 32. At this time, the light intensity distribution of the bifurcated light beam 32 is such that a large intensity of light exists near a divided part (a side derived from a rectilinear part corresponding to the boundary) and a small intensity of light exists near a circumference (a side derived from an outer periphery of the original light beam). The bifurcated light beams 32 do not have to be divided equally but are preferably divided substantially equally so that the light intensity distribution can be made even through overlapping in a subsequent step.

After the light beam 31 is bifurcated in this manner, the respective deformed light beams obtained from bifurcation are transmitted through space such that in the organism irradiation area, the part of the light intensity distribution having a small light intensity is in the center. Although the light diffusion plate 35 is used here, the light diffusion plate 35 does not have to be used. After passing through the light diffusion plate 35, the light beams are refracted by the reflection trapezoidal prism 36 and then caused to enter the organism 39 diagonally from either side while avoiding the ultrasound probe 37. The buffering member 38 is positioned between the ultrasound probe 37 and the organism 39, and the illumination range of the organism surface varies in accordance with the thickness of the buffering member 38. The reflection prism and the reflection trapezoidal prism correspond to a first reflection prism and a second reflection prism of the present invention, respectively.

Figure 4:
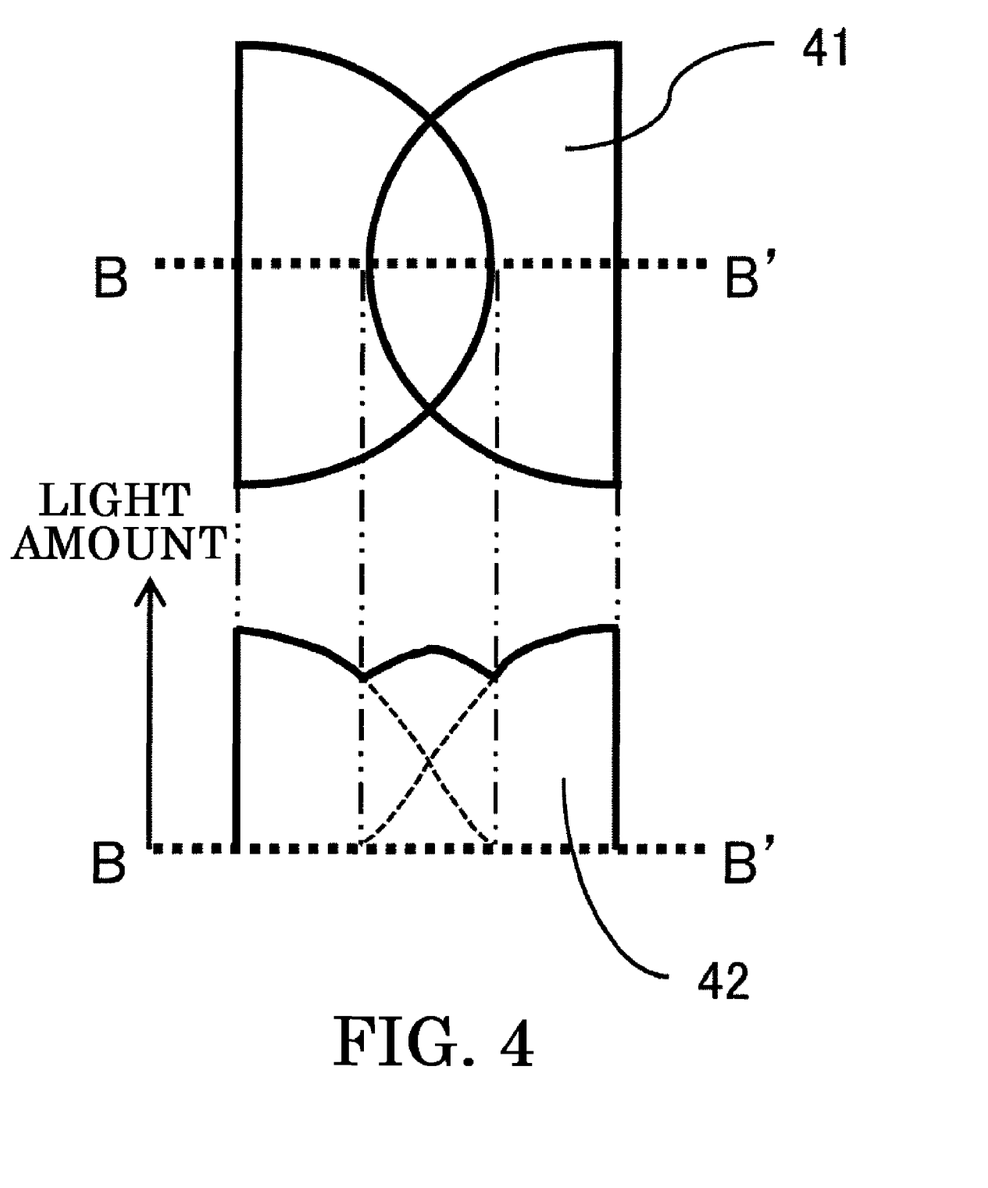
FIG. 4 is a view showing an illumination area and a light intensity distribution obtained when bifurcated light beams are overlapped.

FIG. 4 shows the illumination range and the light intensity distribution on the organism surface. Bifurcated light beams 41 are emitted onto the organism surface with a light intensity distribution 42 on a line B-B' as indicated on a graph. By irradiating the organism surface such that the circumference parts (the outer edge part of the emitted light beam) in which the light intensity is small in the light intensity distribution of the respective bifurcated light beams overlap in this manner, the light intensity distribution difference over the entire irradiation area can be reduced. In this embodiment, the light beam is bifurcated at the part where the light intensity is large. Moreover, the bifurcated light beams 32 are caused to enter the organism surface using the reflection prism 34 and the reflection trapezoidal prism 36 disposed in the light beam transmission area. In the light beam 31, the part of the light beam distribution having a large light intensity is positioned in the center part, i.e. the interior of the light beam, whereas in the organism surface illumination area formed by the bifurcated light beams 32, the part of the light intensity distribution having a large light intensity is positioned on the outside. In other words, the light intensity distribution is inverted. As a result, in this embodiment, a light intensity distribution difference in the irradiation area of the organism surface can be reduced simply and effectively.

(Third Embodiment)

Figure 5:
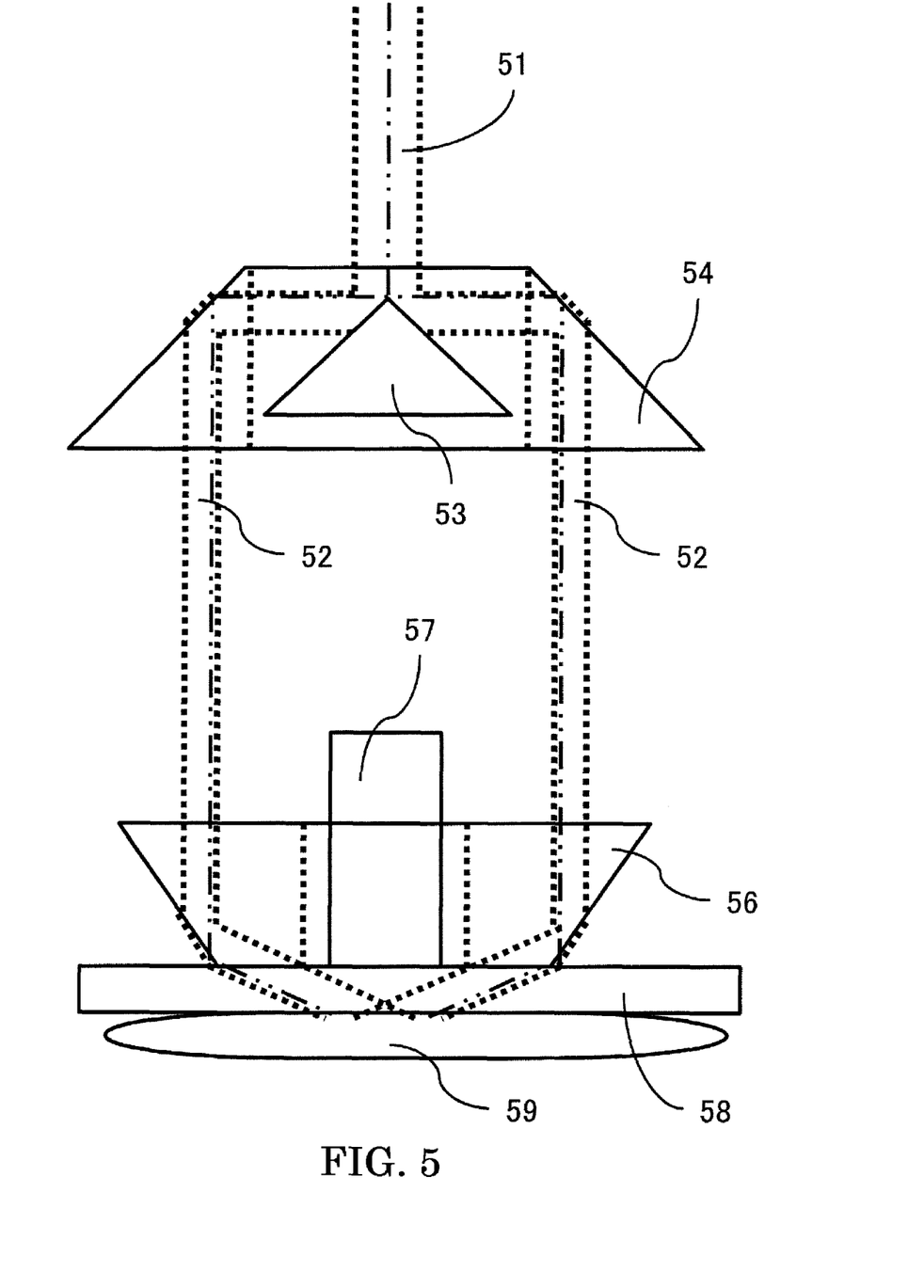
FIG. 5 is a schematic view showing the constitution of an apparatus according to a third embodiment.

FIG. 5 is a schematic view showing an apparatus according to this embodiment. In the drawing, an emitted light beam 51 and a deformed light beam 52 are shown as light beams. Further, a bifurcation conical optical member 53, a reflection optical member 54, and a reflection second optical member 56 are provided as an optical system. Furthermore, an ultrasound probe 57 and a buffering member 58 are disposed to contact an organism 59. This drawing is a sectional view of the apparatus, taken along a plane including the emitted light beam. When seen from an identical direction to the emitted light beam, the bifurcation conical optical member 53 is circular and surrounded by the larger circular reflection optical member 54. Further, when the apparatus is seen from the organism side, the reflection second optical member 56 is also circular, and the probe is positioned directly in the center thereof. A high-energy pulse laser is used as a light source. The emitted light beam is pseudo-circular and has a light intensity distribution in which a large intensity of light exists in a central part of the light beam. In the drawing, outer edges of the light beams are indicated by dotted lines and parts of the light intensity distribution having a large light intensity are indicated by dot-dot-dash lines.

The part of the light beam 51 having a large light intensity is emitted in alignment with an apex of the bifurcation conical optical member 53. The light beam 51 is reflected by a curved surface of the cone to form the deformed light beam 52. The deformed light beam 52 takes a donut shape having a hole in a central part, and the ultrasound probe 57 can be disposed in a space created by the deformation. The deformed light beam 52 enters the organism 59 diagonally around the periphery of the ultrasound probe 57. The buffering member 58 is positioned between the ultrasound probe 57 and the organism 59, and the illumination range of the organism surface varies in accordance with the thickness of the buffering member 58.

The reflection optical member 54 used to reflect the deformed light beam has a hole in its interior, and the entire deformed light beam is reflected by an outer peripheral side face thereof. The reflection second optical member 56 is similar to the reflection optical member 54. Note, however, that the shape of the reflection members is not limited to this example. After being reflected by the reflection optical member 54, the donut-shaped deformed light beam 52 maintains the condition in which a large intensity of light exists in an area near an inside inner periphery. After being reflected by the reflection second optical member, however, the light intensity distribution of the deformed light beam 52 increases in intensity on the outer side. In other words, in the donut-shaped deformed light beam 52 that enters the buffering member 58 diagonally, the light intensity distribution of the inside part decreases such that the interior space gradually grows smaller. By overlapping the parts having a small light intensity on the organism surface, the donut-shaped interior space can be eliminated, and as a result, the light intensity distribution difference can be reduced.

In PTL 1, a light beam is emitted onto an organism using a substantially identical constitution. However, PTL 1 describes a technique using dark field illumination, in which an illuminated part is not formed on the organism surface on a front surface of the ultrasound probe and illumination is not performed by overlapping light beams. Further, the concept of making the light beam even is not described in PTL 1, and therefore PTL 1 differs in essence from the technique of the present invention.

An upper limit value of the irradiance in the irradiation area of the organism surface is defined by the MPE. The MPE on skin is defined as an "average irradiance within a circle having a diameter of 3.5 mm". Hence, in this example, the amount of overlap of the light beams is determined using the "average irradiance within a circle having a diameter of 3.5 mm" in the illumination area of the organism surface as a condition. The average irradiance when the light beams are overlapped is preferably smaller than the aforesaid maximum average irradiance within the entire irradiation area of the organism surface. By limiting the overlap area, a wider area can be irradiated while reducing the light distribution difference.

In most cases, the light beam emitted from the light source exhibits a distribution in which a large light intensity exists in the central part of the light beam. However, in cases where a part having high energy density exists locally in the interior of the light beam and cases where such local parts are eccentrically located, the light beam cannot be evened out favorably using the above method alone. With a high output pulse laser in particular, a laser oscillation mode differs according to the laser constitution, and multi-mode oscillation, in which a large number of modes coexist, is often performed. In multi-mode oscillation, regions in which the energy density is high appear locally in accordance with a distance from an emission port due to interaction between the modes. In this case, an optical member having a diffusion function such as a light diffusion plate is preferably disposed on the path of the bifurcated or deformed light beam. By passing the light beam through the light diffusion plate before it enters the organism, local unevenness can be reduced, leading to an increase in smoothness. By overlapping the light on the organism surface after it passes through the diffusion plate member, a further improvement can be achieved in the evenness of the light intensity distribution over the entire irradiation area, and as a result, the illumination efficiency can be improved.

Example

An example in which a light beam emitted from a light source is bifurcated in two will now be described using the schematic view shown in FIG. 3. In this example, a Ti:sa laser, which is a wavelength variable nanosecond pulse laser capable of oscillating a wavelength in a near infrared area suitable for organism measurement, is used as the light source. The used wavelength is 800 nm. An Nd:YAG laser that performs multi-mode oscillation for obtaining high energy output is used as an excitation laser of the Ti:sa laser. The light beam emitted from the Ti:sa laser is greatly dependent on the shape of a light beam from the Nd:YAG laser used to excite the Ti:sa laser. The light beam from the Ti:sa laser takes a pseudo-circular shape conforming to a columnar Nd:YAG rod. The light intensity distribution of the Ti:sa laser is such that a large intensity of light exists in the center of the light beam.

The emitted laser travels along the path described in the second embodiment using FIG. 3, and enters the organism. More specifically, the pseudo-circular light beam 31 emitted from the laser is divided into two semicircles by the knife edge 45 degree right-angled reflection triangular prism 33 to form the bifurcated light beams 32. The bifurcated light beams 32 are then reflected by the reflection prism 34 and the reflection trapezoidal prism 36 so as to enter the organism diagonally.

In this example, the ultrasound probe 37 is constituted by a two-dimensional array, and therefore the bifurcated light beams 32 enter from both sides of the ultrasound probe 37. The polymethyl pentene buffering member 38 is disposed between the ultrasound probe 37 and the organism 39. After passing through the buffering member 38, the bifurcated light beams 32 enter the organism surface positioned on the front surface of the ultrasound probe 37. The bifurcated beams 32 increase gradually in aperture while passing through the light diffusion plate 35. By passing the bifurcated beams 32 through the light diffusion plate 35, local spot areas having a large light intensity are smoothed.

Here, the semicircular bifurcated light beams 32 are reflected by the reflection prism 34 such that the respective circumference parts thereof move to the outside. The light intensity distribution parts having a large light intensity, meanwhile, are positioned near a straight line forming a divided part, corresponding to the central part of the original light beam 31. The transmitted bifurcated light beams 32 are then reflected by an inclined surface of the reflection trapezoidal prism 36, and as a result, the circumference parts are inverted so as to be oriented inwardly. By causing the bifurcated light beams 32 to enter the organism surface diagonally in this manner, the part of the light intensity distribution having a large light intensity becomes outwardly oriented. The inner sides of the bifurcated light beams 32 entering the organism diagonally, or in other words the respective circumference parts of the semicircular bifurcated light beams 32, are overlapped before entering the organism surface. By overlapping the areas of the bifurcated light beams having a small light intensity in this manner before illuminating the organism, the light intensity in the overlapped part is increased. At this time, the overlap amount is limited to ensure that the light intensity distribution in the overlapped part of the entire illumination area does not reach the maximum light intensity.

In this example, an opening having a diameter of 3.5 mm, as defined by the MPE, was created, the light beam passing through this opening was measured using a power meter in order to measure the irradiance, and the energy emitted from the light source was controlled to remain at or below the MPE. As a result, the maximum irradiance of the light beam passing through the opening diameter of 3.5 mm in the entire illumination area was 30 mJ/cm$^2$, and the average irradiance was 23 mJ/cm$^2$. In a case where the illumination area was formed without overlapping the inner sides of the bifurcated light beams 32 entering the organism diagonally, or in other words the respective circumference parts of the semicircular bifurcated light beams 32, on the other hand, the maximum irradiance of the light beam passing through the opening diameter of 3.5 mm was 30 mJ/cm², and the average irradiance was 18 mJ/cm². Hence, by employing this method, illumination can be performed evenly with a small light intensity distribution difference, and as a result, illumination can be performed effectively using a large total emitted light intensity.

While the present invention has been described with reference to exemplary embodiments, it is to be understood that the invention is not limited to the disclosed exemplary embodiments. The scope of the following claims is to be accorded the broadest interpretation so as to encompass all such modifications and equivalent structures and functions.

This application claims the benefit of Japanese Patent Application No. 2010-101006, filed on Apr. 26, 2010, which is hereby incorporated by reference herein in its entirety.

The invention claimed is:

1. A photoacoustic measuring apparatus comprising:
 a light source which emits a beam of laser light, wherein the beam of laser light has a light intensity distribution in which a large light intensity exists in a central part;
 a forming unit which forms a plurality of second light beams by dividing or deforming the beam of laser light;
 an optical member which guides the second light beams to an irradiation area on a surface of a subject;
 a probe which obtains a photoacoustic wave generated from the subject when the subject is irradiated with the second light beams; and
 a buffering member which contacts the surface of the subject and transmits the laser light,
 wherein said optical member emits the second light beams onto the surface of the subject such that areas of the second light beams having a small light intensity overlap,
 wherein said probe and said optical member are positioned on an identical side of said buffering member relative to the subject,
 wherein said optical member refracts the second light beams such that the second light beams enter the subject through said buffering member while avoiding said probe,
 wherein said forming unit divides the beam of laser light into the plurality of second light beams using the central part as a boundary between the second light beams such that the light intensity is large at a side near the boundary and small at a side nearer to an outer periphery of the beam of laser light, and
 wherein said optical member irradiates the subject with the second light beams such that the sides of the plurality of second light beams having a small light intensity overlap and such that the sides of the plurality of second light beams having a large light intensity do not overlap.

2. The photoacoustic measuring apparatus according to claim 1, wherein an irradiance of the laser light in the irradiation area on the surface of the subject is smaller than a maximum permissible exposure on the surface of the subject.

3. The photoacoustic measuring apparatus according to claim 1, wherein said forming unit is a beam splitter that divides the beam of laser light into the plurality of second light beams while maintaining the light intensity distribution thereof.

4. The photoacoustic measuring apparatus according to claim 1,
 wherein said forming unit is a knife edge prism which divides the beam of laser light into two of the second light beams, and
 wherein said optical member is constituted by a combination of a first reflection prism for inverting the second light beams such that an area having a small light intensity is positioned on an outer side, and a second reflection prism for guiding the inverted second light beams to the irradiation area of the subject.

5. The photoacoustic measuring apparatus according to claim 1, wherein said forming unit is a conical optical member for deforming the laser light into a donut-shaped second light beam as one of the second light beams.

6. The photoacoustic measuring apparatus according to claim 1, further comprising a light diffusion plate that is disposed on a transmission path of the second light beams to smooth a light intensity distribution of the second light beams.

* * * * *